(12) United States Patent
Kown et al.

(10) Patent No.: US 7,829,729 B2
(45) Date of Patent: Nov. 9, 2010

(54) 1-GLYCIDYL-3,3-DINITROAZETIDINE CONTAINING EXPLOSIVE MOIETY AND PREPARATION METHOD THEREOF

(75) Inventors: Young-Hwan Kown, Kyungsan-si (KR); Jin-Seuk Kim, Daejeon-si (KR); Hyoun-Soo Kim, Daejeon-si (KR)

(73) Assignee: Agency for Defense Development, Daejeon-si (KR)

( * ) Notice: Subject to any disclaimer, the term of this patent is extended or adjusted under 35 U.S.C. 154(b) by 214 days.

(21) Appl. No.: 12/333,951

(22) Filed: Dec. 12, 2008

(65) Prior Publication Data
US 2009/0299079 A1 Dec. 3, 2009

(30) Foreign Application Priority Data
May 28, 2008 (KR) ...................... 10-2008-0049625

(51) Int. Cl.
*C07D 405/06* (2006.01)

(52) U.S. Cl. ..................................................... 548/953
(58) Field of Classification Search .................. 548/953
See application file for complete search history.

(56) References Cited

U.S. PATENT DOCUMENTS 7,507,842 B2 * 3/2009 Oehler et al. ............... 549/510

* cited by examiner

*Primary Examiner*—Kamal A Saeed
(74) *Attorney, Agent, or Firm*—Young & Thompson

(57) ABSTRACT

Disclosed is a 1-glycidyl-3,3-dinitroazetidine(GDNAZ) of Formula I wherein dinitroazetidine group which is a high energy group having unit structure of explosive moiety is incorporated to a monomer, and the method thereof. By using the GDNAZ of the present invention in the synthesis of energetic binder for high-performance insensitive explosive, an energetic binder with enhanced thermal and storing stability and explosive power can be provided.

2 Claims, No Drawings

1-GLYCIDYL-3,3-DINITROAZETIDINE CONTAINING EXPLOSIVE MOIETY AND PREPARATION METHOD THEREOF

TECHNICAL FIELD

The present invention relates to an 1-Glycidyl-3,3-dinitroazetidine containing explosive moiety which can be used for high-energy binder of insensitive high performance explosive, and also to the method for preparing the same.

BACKGROUND ART

Recently, Hydroxyl-Terminated Polybutadiene (HTPB), which is a prepolymer of a binder for Plastic-Bonded Explosives (PBX's), has been widely used as a binder for polyurethane groups. This binder is contained in PBX in the amount of about 15% by weight to improve mechanical properties of PBX. However, since this binder is an inert material, it can reduce the energy of PBX.

Therefore, many efforts have been made to develop a high-energy binder(energetic binder) in order to increase the energy of PBX. As a result of such efforts, new types of energetic binders have been developed, which include binders containing energetic explosophoric groups such as nitro (—C—$NO_2$), nitrate (—O—$NO_2$), nitramine (—N—$NO_2$), and azido (—$N_3$) functional groups. More specifically, the energetic binders include poly(glycidyl nitrate) (PGN, formula 1), glycidiyl azide polymer (GAP, formula 2), poly[3,3-bis(azidomethyl)oxetane] (poly[BAMO], formula 3), poly(3-azidomethyl-3-methyloxetane) (poly[AMMO], formula 4) and the like.

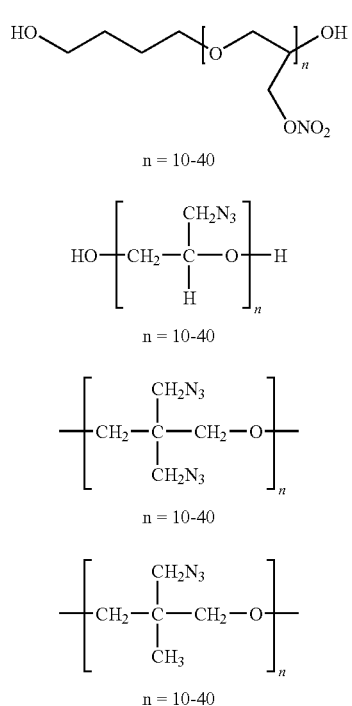

However, many energetic binders containing azido groups such as the GAP of Formula 2, the poly[BAMO] of the Formula 3, and poly[AMMO] of the Formula 4 have not been widely used as energetic binders due to their poor thermal stability and relatively high sensitivity to mechanical stimuli.

A typical example of energetic binders containing nitrate groups is the PGN of Formula 1. But the energetic binders like the PGN are self-decomposed in the polyurethane elastomer, after a polyurethane elastomer has been synthesized, as shown in the following reaction scheme 1.

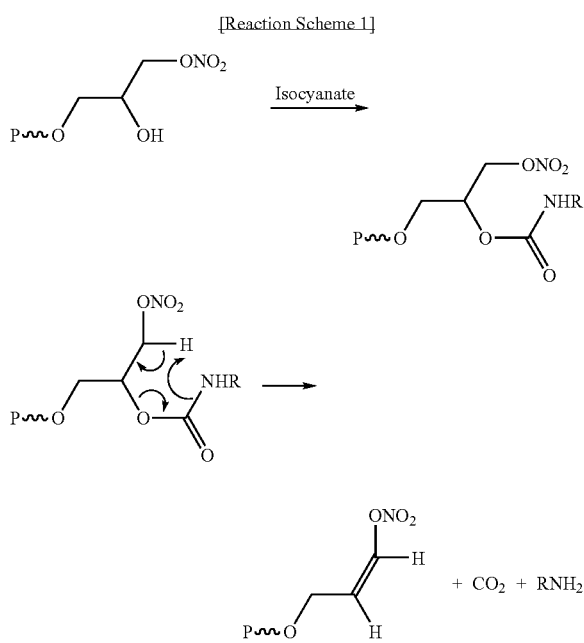

As shown in reaction scheme 1, when the polyurethane elastomer is synthesized by using the PGN of the Formula 1, the hydrogen atom which binds to the carbon to which a nitrate group is bound is chemically acidified thereby causing a decomposition reaction as shown in reaction scheme 1, and thereby causes a decomposition of the main chain of polyurethane.

So far, application of energetic binders containing explosophoric groups such as nitro and nitramine groups has been limited because of difficulty in synthesis. Despite, many researches made in order to solve such problems, no remarkable results have not been obtained yet.

SUMMARY OF THE INVENTION

Therefore, the objective of the present invention is to provide a monomer for high energy binder with improved thermal stability compared to the conventional high energy binder. For this purpose, nitro group is introduced instead of nitrate group in order to improve thermal stability of the high energy binder, and no hydrogen is bound to the carbon to which the nitro group is bound in order to solve the problem of self-decomposition shown in the polyurethane binder produced using the conventional PGN.

DISCLOSURE OF THE INVENTION

In order to achieve the objective of the present invention, provided is a 1-glycidyl-3,3-dinitroazetidine represented by the Formula I.

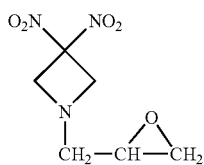

[Formula I]

The method for preparing 1-Glycidyl-3,3-dinitroazetidine according to the present invention, which is represented by the Formula I, comprises the steps of:

(1) reacting 3,3-dinitroazetidine of Formula II with epichlorohydrin of Formula III to obtain 1-chloropropanol-3,3-dinitroazetidine of Formula IV, as shown in the following reaction scheme 2-1; and

[Reaction Scheme 2-1]

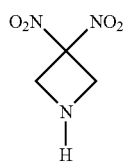

[Formula II]

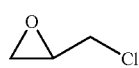

[Formula III]

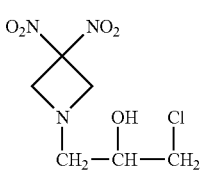

[Formula IV]

(2) reacting 1-chloropropanol-3,3-dinitroazetidine of Formula IV prepared in step (1) with aqueous solution of NaOH to obtain 1-glycidyl-3,3-dinitroazetidine of Formula I, as shown in the following reaction scheme 2-2.

[Reaction Scheme 2-2]

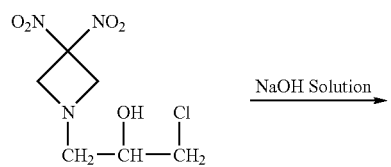

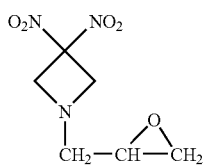

Now, the preferable embodiment of preparing 1-glycidyl-3,3-dinitroazetidine of the present invention is described.

In step (1), epichlorohydrin of Formula III is added dropwise to 3,3-dinitroazetidine of Formula II in diethylether at room temperature. Thus obtained solution is heated to the temperature of 25-50° C. and stirred for 1-5 hours.

In step (2), 1-chloropropanol-3,3-dinitroazetidine of Formula IV prepared in step (1) is cooled, and NaOH aqueous solution is slowly dropped. Thus obtained brown solution is warmed to room temperature and stirred for 3-10 hours. The solution obtained is washed with distilled water and then distilled with diethylether. Thus obtained organic layer is dried on $K_2CO_3$. The solvent is removed under lowered pressure and 1-glycidyl-3,3-dinitroazetidine is obtained.

Effect of the Invention

By using the 1-glycidyl-3,3-dinitroazetidine of the present invention in the synthesis of high-energy binder, the synthesized high-energy binder has improved thermal stability compared to conventional high energy binder and self decomposition is prevented. Also, the explosive to which the high energy binder made from the 1-Glycidyl-3,3-dinitroazetidine of the present invention has high performance and improved stability against external stimulus.

EXAMPLES

Hereinafter, the present invention will be described in more detail with reference to examples. However, the present invention is not limited by the following examples.

Materials

Paraformaldehyde, nitromethane, sodium hydroxide (NaOH), tert-butylamine, hydrochloric acid (HCl), diisopropyl azodicarboxylate (DIAD), triphenyl phosphine ($Ph_3P$), butanone, sodium nitrite($NaNO_2$), potassium ferricyanide ($K_3Fe(CN)_6$), sodium persulfate ($Na_2S_2O_8$), magnesium sulfate ($MgSO_4$), boron trifluoride etherate ($BF_3.OEt_2$), acetic anhydride ($Ac_2O$), sodium bicarbonate ($NaHCO_3$), epichlorohydrin (ECH), and potassium carbonate ($K_2CO_3$) from Sigma-Aldrich Chemical Company were used. Dichloromethane (MC), chloroform, acetone, hexane, methanol and diethyl ether from DaiHan Scientific Co. Ltd (Korea) were used.

The overall procedure of preparing the 1-glycidyl-3,3-dinitroazetidine of the present invention in the following examples is shown in the reaction scheme 3.

[Reaction Scheme 3]

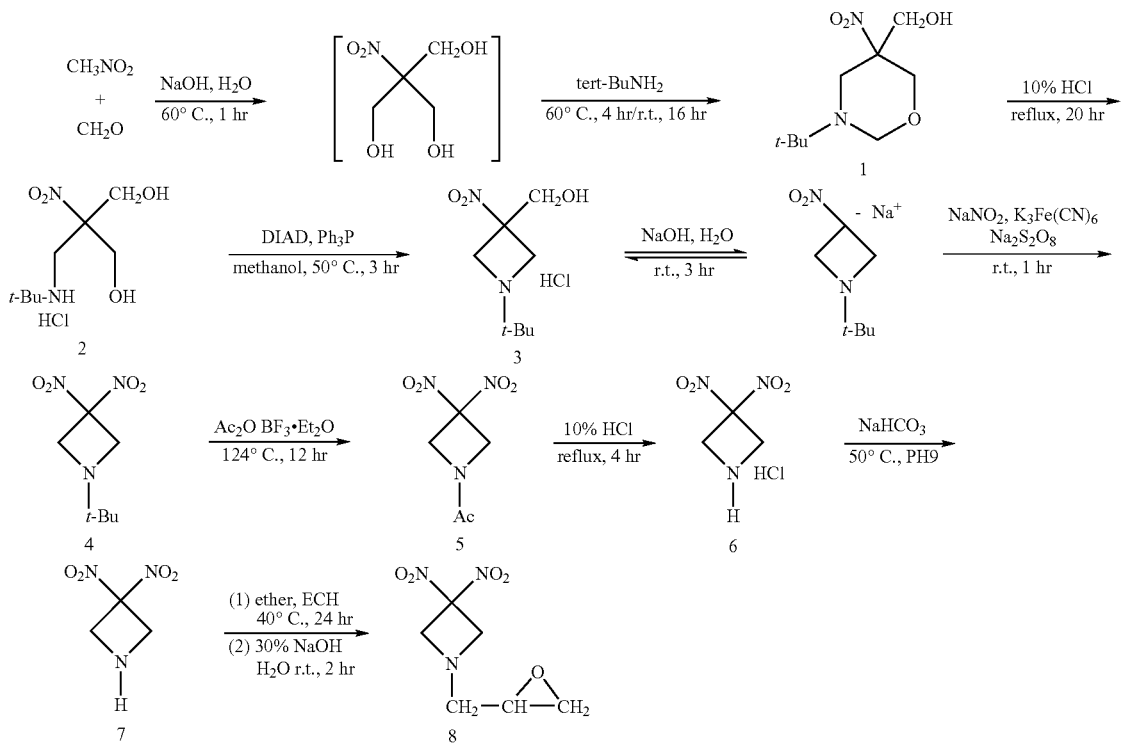

Example 1

Synthesis of N-tert-butyl-5-hydroxymethyl-5-nitrotetrahydroxy-1,3-oxazine

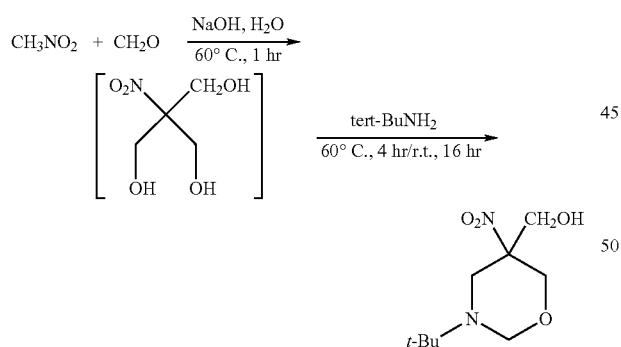

To aqueous solution of paraformaldehyde (48 g, 1.60 mol) and NaOH (24 drops, 40% NaOH) in 240 ml of distilled water, Nitromethane (24 g, 0.39 mol) was added dropwise over 1 hour at 40° C. The resulting solution was heated to 60° C. and stirred for 1 hour. Then tert-butylamine (28.0 g, 0.524 mol) dissolved in 72 ml of distilled water was added dropwise slowly. The precipitate began to appear during the addition. The mixture was then stirred for another 4 hours, cooled to room temperature, and stirred for 16 hours at room temperature. The precipitate was collected by filtrating under lowered pressure at room temperature, washed with distilled water, and vacuum freeze dried to give N-tert-butyl-5-hydroxymethyl-5-nitrotetrahydroxy-1,3-oxazine (69.60 g, 0.319 mol, yield: 81.89%) as a white powder.

NMR analysis:

$^1$H NMR (DMSO-$d_6$): δ 0.98 (s, 9H), 2.63(d, 1H), 3.65 (m, 4H), 3.82 (d, 1H), 4.48 (d, 2H), 5.42 (d, 1H).

$^{13}$C NMR (DMSO-$d_6$): δ 26.8, 49.5, 53.2, 64.9, 68.7, 81.7, 87.7.

Elemental analysis:

Calculated: C-49.53,H-8.31,N-12.84,C/N:3.857.

Measured: C-50.24,H-8.02,N-13.39,C/N:3.752.

Mass analysis: MS (ES+ve) m/z 219 (M+H+): 218, 203, 41.

Example 2

Synthesis of N-tert-butyl-aminomethyl-2-nitro-1,3-propandiol hydro-chloride

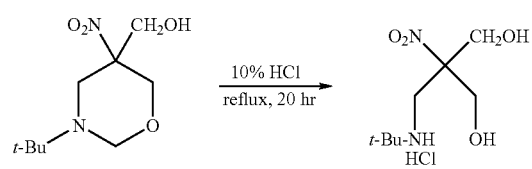

To a solution of concentrated hydrochloric acid (13.42 ml, 0.162 mol) in methanol (125 ml), N-tert-butyl-5-hydroxymethyl-5-nitrotetrahydroxy-1,3-oxazine (34.8 g, 0.160 mol)

prepared in the Example 1 was added. The resulting solution was refluxed for 20 hours. The solvent was removed via vacuum evaporation and the residue was dissolved in isopropyl alcohol (25 ml). The solution was re-crystallized below 0° C. and the precipitate was collected via vacuum filtration, washed with isopropanol and vacuum freeze dried to give the white compound of N-tert-butyl-aminomethyl-2-nitro-1,3-propandiolhydrochloride (24.50 g, 0.101 mol, yield: 63.30%).

Elemental analysis:
Calculated: C-42.8,H-7.63,N-12.47.
Measured: C-42.87 H-7.97 N-12.49.
Mass analysis: MS (ES+ve) m/z 224.7 (M+H+): 188, 173, 110, 126, 86, 57.

Example 4

Synthesis of N-tert-butyl-3,3-dinitroazetidine

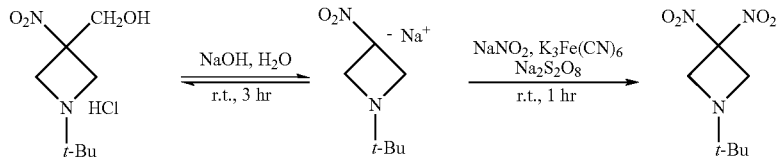

NMR analysis:
$^1$H NMR spectrum (D$_2$O) δ 1.26 (s, 9H), 3.70 (s, 2H), 3.80 (d,2H), 3.99(d, 2H).
$^{13}$C NMR (D$_2$O) δ 24.5, 43.8, 59.2, 63.0, 92.3.
Elemental analysis:
Calculated: C-49.59,H-7.89,N-1.54,C/N:3.428.
Measured: C-39.68,H-8.18,N-11.71,C/N:3.388.
Mass analysis: MS (ES+ve) m/z207 (M+H+): 207, 191, 128, 58.

Example 3

Synthesis of N-tert-butyl-3-hydroxymethyl-3-nitroazetidine hydrochloride

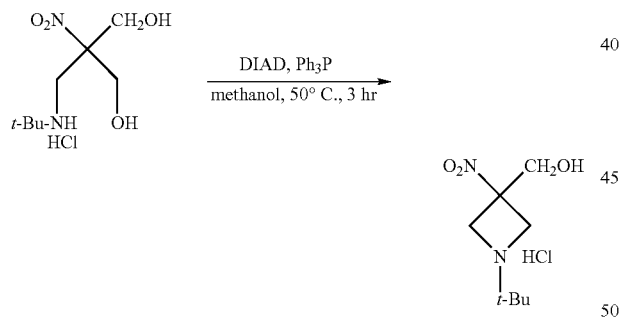

To a solution(40 ml) of diisopropyl azodicarboxylate (DIAD) (23.269 g, 0.1175 mol) and N-tert-butyl-aminomethyl-2-nitro-1,3-propandiol hydrochloride (25.306 g, 0.1044 mol) prepared in the Example 2 in butanone, a minimum amount of a solution of triphenylphosphine (Ph$_3$P) (29.89 g, 0.132 mol) in butanone was added dropwise over 1 hour at 50° C. while maintaining the temperature of the solution at 50-55° C. The resultant was stirred at 50° C. for 3 hours, filtered, washed with cold butanone (30 ml) and vacuum freeze dried to give N-tert-butyl-3-hydroxymethyl-3-nitroazetidine hydrochloride (15.647 g, 0.070 mol, yield: 67.02%) as a white solid.
NMR analysis:
$^1$H NMR (D$_2$O) δ 1.35 (s, 9H), 4.25 (s, 2H), 4.50 (s, 1H), 4.84(s, 6H).
$^{13}$C NMR (D$_2$O) δ 21.70, 53.1, 60.2, 62.0, 80.8.

To a solution (60 ml) of N-tert-butyl-3-hydroxymethyl-3-nitroazetidine hydrochloride (13.50 g, 0.060 mol) prepared in the Example 3 in distilled water, 30 ml of aqueous solution of NaOH (7.173 g, 0.179 mol) was added. The resulting yellow solution was stirred for 3 hours at room temperature. The resultant was cooled to 8° C. and a chilled solution (45 ml) of sodium nitrite (NaNO$_2$) (16.5 g, 0.239 mol) and potassium ferrocyanide (K$_3$Fe(CN)$_6$) (1.974 g, 0.060 mol) in distilled water was added slowly. Then, solid sodium persulphate (Na$_2$S$_2$O$_8$) (17.80 g, 0.075 mol) was added in a single portion. The resulting yellow solution was warmed to room temperature as the solution gradually turned into light orange color. The solution was stirred for another 1 hour and then extracted with dichloromethane (CH$_2$Cl$_2$) (150 ml). The organic layer was dried with magnesium sulfate (MgSO$_4$) and the solvent was removed via vacuum evaporation to give N-tert-butyl-3,3-dinitroazetidine (12.583 g, 0.062 mol, yield: 86.66%) as a yellow oil.
NMR analysis:
$^1$H NMR (CDCl$_3$) δ 1.0 (s, 9H), 4.06(s, 4H).
$^{13}$C NMR (CDCl$_3$) δ 23.7, 52.7, 55.2, 107.8.
Elemental analysis:
Calculated: C-41.38,H-6.45,N-20.68,C/N: 1.997.
Measured: C-41.68,H-5.30,N-19.91,C/N: 2.108.
Mass analysis: MS (ES+ve) m/z204(M+H+): 203, 188, 157, 142, 86.

Example 5

Synthesis of N-acetyl-3,3-dinitroazetidine

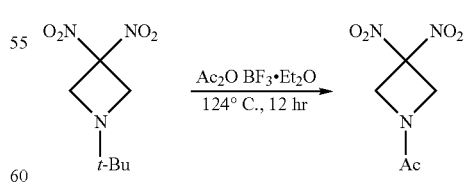

To N-tert-butyl-3,3-dinitroazetidine (12.95 g, 0.064 mol) prepared in the Example 4,acetic anhydride (25.06 ml) was slowly added, followed by boron trifluoride etherate (0.085 ml) using syringe. The mixture was reacted at 124° C. for 12 hours under nitrogen atmosphere. Excess acetic anhydride was removed by vacuum distillation. The resultant was dissolved in chloroform and re-crystallized to give N-acetyl-3,3-dinitroazetidine (11.26 g, 0.060 mol, yield: 93.38%) as a crystal.

NMR analysis:
$^1$H NMR (CDCl$_3$) δ 2.06(s, 3H), 4.78 (s, 2H), 4.96 (s, 2H).
$^{13}$C NMR (CDCl$_3$) δ 23.7, 52.7, 55.2, 107.8.
Elemental analysis:
Calculated: C-31.75,H-3.73,N-22.22,C/N: 1.997.
Measured: C-33.57,H-4.54,N-20.08,C/N:1.672.
Mass analysis: MS (ES+ve) m/z189(M+H+): 189, 142, 101, 86, 43.

Example 6

Synthesis of 3,3-dinitroazetidine hydrochloride

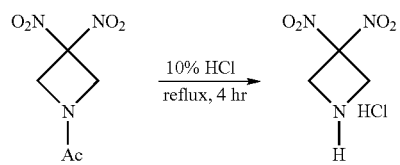

To a solution (20 ml) of N-acetyl-3,3-dintroazetidine (2.987 g, 0.016 mol) prepared in the Example 5 in distilled water, aqueous solution of hydrochloric acid (10 wt %, 30 ml) was added dropwise. The resulting solution was stirred under gentle reflux for 4 hours. The solvent was removed under lowered pressure to give 3,3-dintroazetidine hydrochloride (2.328 g, yield: 80.25%) as a white solid.

NMR analysis:
$^1$H NMR (DMSO) δ 4.92 (s, 4H).
$^{13}$C NMR (DMSO) δ 52.8, 107.3.
Elemental analysis:
Calculated: C-19.63,H-3.29,N-22.89,C/N: 0.858.
Measured: C-20.34,H-4.07,N-20.34,C/N:1.014.
Mass analysis: MS (ES+ve) m/z 183.5 (M+H+): 147, 100, 54, 72, 42.

Example 7

Synthesis of 3,3-dinitroazetidine(DNAZ)

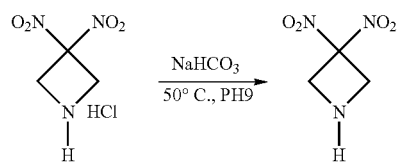

3,3-dintroazetidine hydrochloride (1.508 g, 8.217 mmol) prepared in the Example 6 was dissolved in distilled water (50 ml), then the solution was heated to 50° C. Aqueous solution of sodium hydrogencarbonate (NaHCO$_3$) (10 wt %) was slowly added dropwise until the pH value of the solution reached 9. The resulting solution was extracted with chloroform (each 20 ml) three times, and the organic layer was dried with magnesium sulfate (MgSO$_4$). The solvent was removed under lowered pressure to give 3,3-dintroazetidine as a light yellow oil (0.670 g, 4.557 mol, yield: 55.47%).

NMR analysis:
$^1$H NMR (D$_2$O) δ 4.55 (m, 4H).
$^{13}$C NMR (D$_2$O) δ 54.1, 111.1.
Elemental analysis:
Calculated: C-24.50,H-3.43,N-28.57,C/N: 0.858.
Measured: C-25.40,H-3.85,N-27.45,C/N: 0.925.
Mass analysis: MS (ES+ve) m/z 147 (M+H+): 147, 100, 54, 72, 42.

Example 8

Synthesis of 1-glycidyl-3,3-dinitroazetidine(GDNAZ)

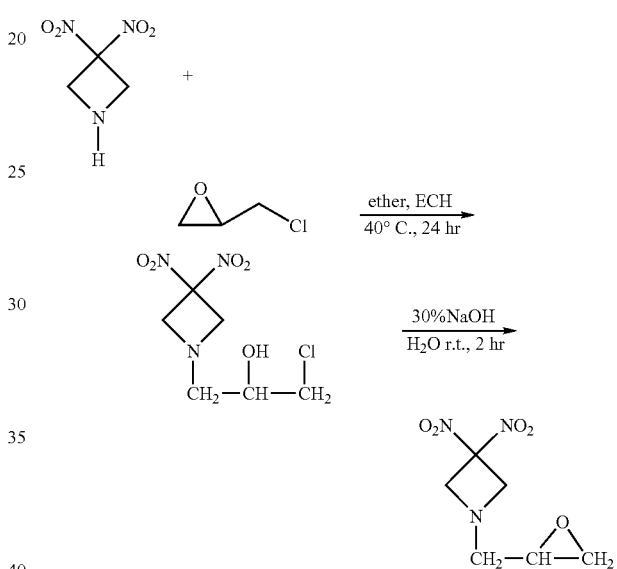

To a solution of DNAZ (0.723 g, 4.918 mmol) prepared in the Example 7 in diethyl ether ml), epichlorohydrin (ECH) (0.326 ml) was added dropwise. The resulting solution was heated to 40° C. and stirred for 24 hours. After cooling the solution to 8° C., aqueous solution of sodium hydroxide (NaOH) (30 wt %) (0.295 g, 7.375 mmol) was added dropwise slowly. The resulting brown solution was warmed to room temperature slowly and stirred for 2 hours. The solution was washed with distilled water (30 ml) and extracted with diethyl ether (each 20 ml) three times. The organic layer was dried with potassium carbonate (K$_2$CO$_3$). The solvent was removed under lowered pressure to give 1-glycidyl-3,3-dinitroazetidine (GDNAZ) as a light yellow oil (0.485 g, 2.390 mmol, yield: 48.60%).

NMR analysis:
$^1$H NMR (D$_2$O) δ 2.64 (m,1H), 2.85(m,1H), 3.22(s,1H), 3.58(m,2H), 4.20(m, 2H), 4.48(m,2H).
$^{13}$C NMR (D$_2$O) δ 46.9, 51.3, 55.2, 62.3.
Elemental analysis:
Calculated: C-38.36,H-5.98,N-27.45,C/N: 1.397.
Measured: C-37.94,H-5.85,N-28.54,C/N: 1.329.
Mass analysis: MS (ES+ve) m/z203 (M+H+): 160, 42.

What is claimed is:

1. 1-Glycidyl-3,3-dinitroazetidine represented by formula I:

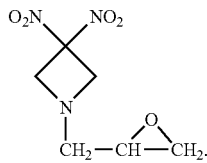

[Formula I]

2. A method for preparing 1-glycidyl-3,3-dinitroazetidine represented by the formula I:

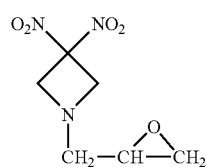

[Formula I]

Wherein the method comprises the steps of:
(1) reacting 3,3-dinitroazetidine of Formula II with epichlorohydrin of Formula III to obtain 1-chloropropanol-3,3-dinitroazetidine of Formula IV; and

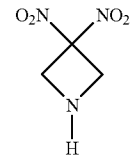

[Formula II]

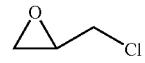

[Formula III]

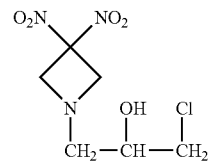

[Formula IV]

(2) reacting 1-chloropropanol-3,3-dinitroazetidine of Formula IV prepared in step (1) with aqueous solution of NaOH to obtain 1-glycidyl-3,3-dinitroazetidine of Formula I.

* * * * *